(12) United States Patent
Hopman et al.

(10) Patent No.: US 7,272,428 B2
(45) Date of Patent: *Sep. 18, 2007

(54) WIRELESS ELECTROCARDIOGRAPH SYSTEM AND METHOD

(75) Inventors: Nicholas C. Hopman, Lake Zurich, IL (US); Daniel L. Williams, Norwell, MA (US); Franco Lodato, Weston, FL (US)

(73) Assignee: Motorola, Inc., Schaumburg, IL (US)

( * ) Notice: Subject to any disclaimer, the term of this patent is extended or adjusted under 35 U.S.C. 154(b) by 416 days.

This patent is subject to a terminal disclaimer.

(21) Appl. No.: 10/439,574

(22) Filed: May 16, 2003

(65) Prior Publication Data

US 2003/0199777 A1    Oct. 23, 2003

Related U.S. Application Data

(63) Continuation of application No. 09/908,509, filed on Jul. 17, 2001, now Pat. No. 6,611,705.

(60) Provisional application No. 60/219,082, filed on Jul. 18, 2000.

(51) Int. Cl.
*A61N 1/04* (2006.01)

(52) U.S. Cl. ..................................... 600/382

(58) Field of Classification Search ................ 600/382, 600/386, 390
See application file for complete search history.

(56) References Cited

U.S. PATENT DOCUMENTS

| | | | |
|---|---|---|---|
| 2,864,943 A | 12/1958 | Schultz | 250/15 |
| 2,958,781 A | 11/1960 | Marchal et al. | 250/83.3 |
| 3,199,508 A | 8/1965 | Roth | 128/2.06 |
| 3,495,584 A | 2/1970 | Schwalm | 128/2.06 |
| 3,602,215 A | 8/1971 | Parnell | 128/2.06 B |
| 3,603,881 A | 9/1971 | Thornton | 325/30 |

(Continued)

FOREIGN PATENT DOCUMENTS

EP    0212278    3/1987

(Continued)

OTHER PUBLICATIONS

Performance Specification sheet published for Motorola C.O.R HT-220 Handie-Talkie FM Radio, printed 1973 by Motorola, 2 pages.

(Continued)

*Primary Examiner*—Scott M. Getzow
(74) *Attorney, Agent, or Firm*—Brinks Hofer Gilson & Lione

(57) ABSTRACT

A method and system for wireless ECG monitoring is provided. An electrode connector, transmitter and receiver operate with existing electrodes and ECG monitors. The electrode connector includes connectors for attaching to disposable or reusable single electrodes. The transmitter transmits the signals from the electrodes to the receiver. The receiver passes the electrode signals to the ECG monitor for processing. ECG monitors used with an electrical conductor, for example wire connections to electrodes, are connected with the receiver, avoiding the purchase of a new monitor. Any legacy ECG monitor, including different ECG monitors, connects with the receiver using the ECG monitor's lead-wires. The ECG monitor operates as if directly connected to the electrodes without the problems discussed above associated with wires running from the ECG monitor to the patient.

19 Claims, 5 Drawing Sheets

U.S. PATENT DOCUMENTS

| | | | |
|---|---|---|---|
| 3,727,190 A | 4/1973 | Vogelman et al. | 340/172.5 |
| 3,729,708 A | 4/1973 | Wolfer et al. | 340/146.1 F |
| 3,757,778 A | 9/1973 | Graham | 128/2.06 R |
| 3,774,594 A | 11/1973 | Huszar | 128/2.06 R |
| 3,810,102 A | 5/1974 | Parks, III et al. | 340/172.5 |
| 3,830,228 A | 8/1974 | Foner | 128/2.06 R |
| 3,834,373 A | 9/1974 | Sato | 128/2.06 E |
| 3,905,364 A | 9/1975 | Cudahy et al. | 128/2.06 R |
| 3,925,762 A | 12/1975 | Heitlinger et al. | 340/150 |
| 3,943,918 A | 3/1976 | Lewis | 128/2.1 A |
| 3,949,397 A | 4/1976 | Wagner et al. | 343/6.5 R |
| 3,970,996 A | 7/1976 | Yasaka et al. | 340/172.5 |
| 3,986,498 A | 10/1976 | Lewis | 128/2.06 R |
| 3,998,213 A | 12/1976 | Price | |
| 4,027,663 A | 6/1977 | Fischler et al. | 128/2.06 R |
| 4,042,906 A | 8/1977 | Ezell | 340/15.5 TS |
| 4,051,522 A | 9/1977 | Healy et al. | 358/86 |
| 4,074,228 A | 2/1978 | Jonscher | 340/146.1 AQ |
| 4,121,573 A | 10/1978 | Crovella et al. | 128/2.1 A |
| 4,124,894 A | 11/1978 | Vick et al. | 364/417 |
| 4,141,351 A | 2/1979 | James et al. | 128/2.06 R |
| 4,150,284 A | 4/1979 | Trenkler et al. | 250/199 |
| 4,156,867 A | 5/1979 | Bench et al. | 340/146.1 |
| 4,173,221 A | 11/1979 | McLaughlin et al. | 128/696 |
| 4,173,971 A | 11/1979 | Karz | 128/702 |
| 4,186,749 A | 2/1980 | Fryer | 128/748 |
| 4,216,462 A | 8/1980 | McGrath et al. | 340/150 |
| 4,233,241 A | 11/1980 | Kalopissis et al. | 564/221 |
| 4,237,900 A | 12/1980 | Schulman et al. | 128/630 |
| 4,260,951 A | 4/1981 | Lewyn | 328/165 |
| 4,262,632 A | 4/1981 | Hanton et al. | 119/1 |
| 4,281,664 A | 8/1981 | Duggan | 128/696 |
| 4,321,933 A | 3/1982 | Baessler | 128/736 |
| 4,353,372 A | 10/1982 | Ayer | 128/640 |
| 4,381,012 A * | 4/1983 | Russek | 600/382 |
| 4,396,906 A | 8/1983 | Weaver | 340/347 DD |
| 4,425,921 A | 1/1984 | Fujisaki et al. | 128/690 |
| 4,441,498 A | 4/1984 | Nordling | 128/419 P |
| 4,449,536 A | 5/1984 | Weaver | 128/696 |
| 4,471,786 A | 9/1984 | Inagaki et al. | 128/748 |
| 4,475,208 A | 10/1984 | Ricketts | 375/1 |
| 4,510,495 A | 4/1985 | Sigrimis et al. | 340/825.54 |
| 4,521,918 A | 6/1985 | Challen | 455/343 |
| 4,531,526 A | 7/1985 | Genest | 128/630 |
| 4,537,200 A | 8/1985 | Widrow | 128/696 |
| 4,556,061 A | 12/1985 | Barreras et al. | 128/419 PT |
| 4,556,063 A | 12/1985 | Thompson et al. | 128/419 PT |
| 4,562,840 A | 1/1986 | Batina et al. | 128/419 PT |
| 4,573,026 A | 2/1986 | Curtis et al. | 332/18 |
| 4,583,548 A | 4/1986 | Schmid | 128/639 |
| 4,583,549 A | 4/1986 | Manoli | 128/640 |
| 4,585,004 A | 4/1986 | Brownlee | 128/419 PT |
| 4,586,508 A | 5/1986 | Batina et al. | 128/419 PG |
| 4,598,281 A | 7/1986 | Maas | 340/664 |
| 4,599,723 A | 7/1986 | Eck | 371/47 |
| 4,601,043 A | 7/1986 | Hardt et al. | 375/1 |
| 4,606,352 A | 8/1986 | Geddes et al. | 128/702 |
| 4,618,861 A | 10/1986 | Gettens et al. | 340/825.54 |
| 4,625,733 A | 12/1986 | Saynajakangas | 128/687 |
| RE32,361 E | 2/1987 | Duggan | 128/696 |
| 4,653,068 A | 3/1987 | Kadin | 375/1 |
| 4,681,118 A | 7/1987 | Asai et al. | 128/643 |
| 4,709,704 A | 12/1987 | Lukasiewicz | 128/644 |
| 4,724,435 A | 2/1988 | Moses et al. | 340/870.13 |
| 4,747,413 A | 5/1988 | Bloch | 128/736 |
| 4,754,483 A | 6/1988 | Weaver | 381/36 |
| 4,783,844 A | 11/1988 | Higashiyama et al. | 455/34 |
| 4,784,162 A | 11/1988 | Ricks et al. | 128/903 |
| 4,791,933 A | 12/1988 | Asai et al. | 128/640 |
| 4,793,532 A | 12/1988 | Leckband et al. | 364/413.06 |
| 4,799,059 A | 1/1989 | Grindahl et al. | 340/870.03 |
| 4,802,222 A | 1/1989 | Weaver | 381/35 |
| 4,803,625 A | 2/1989 | Fu et al. | 364/413.03 |
| 4,805,631 A | 2/1989 | Foi du Maroc, II. | 128/710 |
| 4,835,372 A | 5/1989 | Gombrich et al. | 235/375 |
| 4,839,806 A | 6/1989 | Goldfischer et al. | 364/413.02 |
| 4,850,009 A | 7/1989 | Zook et al. | 379/96 |
| 4,860,759 A | 8/1989 | Kahn et al. | 128/668 |
| 4,865,044 A | 9/1989 | Wallace et al. | 128/736 |
| 4,883,064 A | 11/1989 | Olson et al. | 128/696 |
| 4,889,131 A | 12/1989 | Salem et al. | 128/671 |
| 4,889,132 A | 12/1989 | Hutcheson et al. | 128/680 |
| 4,907,248 A | 3/1990 | Bretl | 375/27 |
| 4,909,260 A | 3/1990 | Salem et al. | |
| 4,916,441 A | 4/1990 | Gombrich | 340/712 |
| 4,928,187 A | 5/1990 | Rees | 360/40 |
| 4,955,075 A | 9/1990 | Anderson | 455/182 |
| 4,957,109 A | 9/1990 | Groeger et al. | |
| 4,958,645 A | 9/1990 | Cadell et al. | 128/903 |
| 4,966,154 A | 10/1990 | Cooper et al. | 128/671 |
| 4,974,607 A | 12/1990 | Miwa | 128/904 |
| 4,981,141 A | 1/1991 | Segalowitz | |
| 5,012,411 A | 4/1991 | Policastro et al. | 364/413.06 |
| 5,025,452 A | 6/1991 | Sohner et al. | 375/1 |
| 5,025,808 A | 6/1991 | Hafner | 128/696 |
| 5,036,462 A | 7/1991 | Kaufman et al. | 364/413.01 |
| 5,036,869 A | 8/1991 | Inahara | 128/903 |
| 5,042,498 A | 8/1991 | Dukes | 128/696 |
| 5,051,799 A | 9/1991 | Paul et al. | 375/25 |
| 5,072,383 A | 12/1991 | Brimm et al. | 364/413.02 |
| 5,077,753 A | 12/1991 | Grau | 375/1 |
| 5,078,134 A | 1/1992 | Heilman et al. | 128/421 |
| 5,085,224 A | 2/1992 | Galen et al. | 128/696 |
| 5,109,845 A | 5/1992 | Yuuchi et al. | 128/421 |
| 5,113,869 A | 5/1992 | Nappholz et al. | 128/696 |
| 5,127,404 A | 7/1992 | Wyborny et al. | 128/419 P |
| 5,131,399 A | 7/1992 | Sciarra | 128/671 |
| 5,137,022 A | 8/1992 | Henry | 128/419 PT |
| 5,153,584 A | 10/1992 | Engira | 340/870.18 |
| 5,157,604 A | 10/1992 | Axford et al. | 364/413.03 |
| 5,168,874 A | 12/1992 | Segalowitz | 128/639 |
| 5,171,977 A | 12/1992 | Morrison | 235/375 |
| 5,177,765 A | 1/1993 | Holland et al. | 375/1 |
| 5,177,766 A | 1/1993 | Holland et al. | 375/1 |
| 5,179,569 A | 1/1993 | Sawyer | 375/1 |
| 5,179,571 A | 1/1993 | Schilling | 375/1 |
| 5,181,519 A | 1/1993 | Bible | 128/704 |
| 5,192,949 A | 3/1993 | Suzuki et al. | 341/68 |
| 5,205,294 A | 4/1993 | Flach et al. | 128/696 |
| 5,212,476 A | 5/1993 | Maloney | 340/825.19 |
| 5,212,715 A | 5/1993 | Pickert et al. | 375/114 |
| 5,224,485 A | 7/1993 | Powers et al. | 128/696 |
| 5,226,431 A | 7/1993 | Bible et al. | 128/904 |
| 5,238,001 A | 8/1993 | Gallant et al. | 128/700 |
| 5,270,811 A | 12/1993 | Ishibashi et al. | 358/108 |
| 5,272,477 A | 12/1993 | Tashima et al. | 340/870.16 |
| 5,292,343 A | 3/1994 | Blanchette et al. | 607/32 |
| 5,305,202 A | 4/1994 | Gallant et al. | 364/413.06 |
| 5,305,353 A | 4/1994 | Weerackody | 375/100 |
| 5,307,372 A | 4/1994 | Sawyer et al. | 375/1 |
| 5,307,817 A | 5/1994 | Guggenbuhl et al. | 128/696 |
| 5,307,818 A | 5/1994 | Segalowitz | 128/696 |
| 5,309,920 A | 5/1994 | Gallant et al. | 128/710 |
| 5,314,450 A | 5/1994 | Thompson | 607/32 |
| 5,335,664 A | 8/1994 | Nagashima | 128/696 |
| 5,339,824 A | 8/1994 | Engira | 128/712 |
| 5,342,408 A | 8/1994 | deCoriolis et al. | 607/32 |
| 5,343,869 A | 9/1994 | Pross et al. | 128/700 |
| 5,348,008 A | 9/1994 | Bornn et al. | 128/642 |
| 5,353,791 A | 10/1994 | Tamura et al. | 128/633 |
| 5,353,793 A | 10/1994 | Bornn | |
| 5,354,319 A | 10/1994 | Wyborny et al. | 607/32 |
| 5,359,641 A | 10/1994 | Schull et al. | 379/106 |
| 5,365,530 A | 11/1994 | Yoshida | 371/37.4 |

| Patent No. | Date | Inventor(s) | Class |
|---|---|---|---|
| 5,375,604 A | 12/1994 | Kelly et al. | 128/671 |
| 5,377,222 A | 12/1994 | Sanderford, Jr. | 375/1 |
| 5,381,798 A | 1/1995 | Burrows | 128/696 |
| 5,392,771 A | 2/1995 | Mock et al. | 128/205.23 |
| 5,394,879 A | 3/1995 | Gorman | |
| 5,394,882 A | 3/1995 | Mawhinney | 128/721 |
| 5,400,794 A | 3/1995 | Gorman | |
| 5,416,695 A | 5/1995 | Stutman et al. | 364/413.02 |
| 5,417,222 A | 5/1995 | Dempsey et al. | 128/696 |
| 5,438,329 A | 8/1995 | Gastouniotis et al. | 340/870.02 |
| 5,438,607 A | 8/1995 | Przygoda, Jr. et al. | 379/38 |
| 5,441,047 A | 8/1995 | David et al. | 128/670 |
| 5,444,719 A | 8/1995 | Cox et al. | 371/37.1 |
| 5,445,149 A * | 8/1995 | Rotolo et al. | 600/382 |
| 5,458,123 A | 10/1995 | Unger | 128/696 |
| 5,458,124 A | 10/1995 | Stanko et al. | 128/696 |
| 5,464,021 A | 11/1995 | Birnbaum | 128/696 |
| 5,485,848 A | 1/1996 | Jackson et al. | 128/672 |
| 5,491,474 A | 2/1996 | Suni et al. | 340/870.31 |
| 5,507,035 A | 4/1996 | Bantz et al. | 455/133 |
| 5,511,553 A | 4/1996 | Segalowitz | 128/696 |
| 5,522,396 A | 6/1996 | Langer et al. | 128/696 |
| 5,524,637 A | 6/1996 | Erickson | 128/779 |
| 5,538,007 A | 7/1996 | Gorman | |
| 5,544,649 A | 8/1996 | David et al. | 128/630 |
| 5,544,661 A | 8/1996 | Davis et al. | 128/700 |
| 5,546,950 A * | 8/1996 | Schoeckert et al. | 600/508 |
| 5,549,113 A | 8/1996 | Halleck et al. | 128/671 |
| 5,564,429 A | 10/1996 | Bornn et al. | 128/696 |
| 5,576,952 A | 11/1996 | Stutman et al. | 364/413.02 |
| 5,579,001 A | 11/1996 | Dempsey et al. | 340/870.01 |
| 5,579,378 A | 11/1996 | Arlinghaus, Jr. | 379/106 |
| 5,579,775 A | 12/1996 | Dempsey et al. | 128/670 |
| 5,579,781 A | 12/1996 | Cooke | 128/733 |
| 5,582,180 A | 12/1996 | Manset et al. | 128/696 |
| 5,586,552 A | 12/1996 | Sakai | 128/633 |
| 5,617,871 A | 4/1997 | Burrows | 128/696 |
| 5,628,324 A | 5/1997 | Sarbach | 128/670 |
| 5,628,326 A | 5/1997 | Arand et al. | |
| 5,634,468 A | 6/1997 | Platt et al. | |
| 5,640,953 A | 6/1997 | Bishop et al. | 128/630 |
| 5,646,701 A | 7/1997 | Duckworth et al. | 340/825.69 |
| 5,664,270 A | 9/1997 | Bell et al. | 5/600 |
| 5,669,391 A | 9/1997 | Williams | |
| 5,678,545 A | 10/1997 | Stratbucker | 128/640 |
| 5,678,562 A | 10/1997 | Sellers | 128/710 |
| 5,685,303 A | 11/1997 | Rollman et al. | 128/644 |
| 5,694,940 A | 12/1997 | Unger et al. | 128/696 |
| 5,704,351 A | 1/1998 | Mortara et al. | |
| 5,718,234 A | 2/1998 | Warden et al. | 128/696 |
| 5,720,771 A | 2/1998 | Snell | 607/60 |
| 5,738,102 A | 4/1998 | Lemelson | 128/671 |
| 5,748,103 A | 5/1998 | Flach et al. | 340/870.07 |
| 5,755,230 A | 5/1998 | Schmidt et al. | 128/731 |
| 5,759,199 A | 6/1998 | Snell et al. | 604/60 |
| 5,767,791 A | 6/1998 | Stoop et al. | 340/870.11 |
| 5,779,630 A | 7/1998 | Fein et al. | 600/323 |
| 5,788,633 A | 8/1998 | Mahoney | 600/382 |
| 5,800,204 A | 9/1998 | Niitsu | 439/495 |
| 5,813,404 A | 9/1998 | Devlin et al. | 128/639 |
| 5,819,740 A | 10/1998 | Muhlenberg | 128/696 |
| 5,820,567 A | 10/1998 | Mackie | 600/519 |
| 5,827,179 A | 10/1998 | Lichter et al. | 600/300 |
| 5,862,803 A | 1/1999 | Besson et al. | |
| 5,865,733 A | 2/1999 | Malinouskas et al. | 600/300 |
| 5,868,671 A | 2/1999 | Mahoney | 600/382 |
| 5,871,451 A | 2/1999 | Unger et al. | 600/509 |
| 5,873,369 A | 2/1999 | Laniado et al. | 128/903 |
| 5,882,300 A | 3/1999 | Malinouskas et al. | 600/300 |
| 5,899,928 A | 5/1999 | Sholder et al. | 607/27 |
| 5,899,931 A | 5/1999 | Deschamp et al. | 607/60 |
| 5,913,827 A | 6/1999 | Gorman | |
| 5,917,414 A | 6/1999 | Oppelt et al. | 340/573.1 |
| 5,919,141 A | 7/1999 | Money et al. | 600/513 |
| 5,919,214 A | 7/1999 | Ciciarelli et al. | 607/32 |
| 5,931,791 A | 8/1999 | Saltzstein et al. | 600/513 |
| 5,935,078 A | 8/1999 | Feierbach | 600/509 |
| 5,938,597 A | 8/1999 | Stratbucker | |
| 5,944,659 A | 8/1999 | Flach et al. | 600/300 |
| 5,949,352 A | 9/1999 | Ferrari | 340/870 |
| 5,954,536 A | 9/1999 | Fuerst et al. | 439/493 |
| 5,954,539 A | 9/1999 | Hornung | 439/590 |
| 5,954,719 A | 9/1999 | Chen et al. | 606/42 |
| 5,957,854 A | 9/1999 | Besson et al. | |
| 5,959,529 A | 9/1999 | Kail, IV | 340/539 |
| 5,960,119 A | 9/1999 | Echigo et al. | 382/248 |
| 5,961,448 A | 10/1999 | Swenson et al. | 600/301 |
| 5,963,650 A | 10/1999 | Simionescu et al. | 380/49 |
| 5,964,701 A | 10/1999 | Asada et al. | 600/300 |
| 5,966,692 A | 10/1999 | Langer et al. | 705/3 |
| 5,970,105 A | 10/1999 | Dacus | 375/344 |
| 5,995,861 A | 11/1999 | Price | 600/372 |
| 5,999,857 A | 12/1999 | Weijand et al. | 607/60 |
| 6,006,125 A | 12/1999 | Kelly et al. | 600/382 |
| 6,009,350 A | 12/1999 | Renken | 607/32 |
| 6,010,359 A | 1/2000 | Etters et al. | 439/496 |
| 6,027,363 A | 2/2000 | Watt et al. | 439/456 |
| 6,039,600 A | 3/2000 | Etters et al. | 439/496 |
| 6,047,201 A | 4/2000 | Jackson, III | 600/344 |
| 6,053,887 A | 4/2000 | Levitas et al. | 604/49 |
| 6,057,758 A | 5/2000 | Dempsey et al. | 340/539 |
| 6,066,093 A | 5/2000 | Kelly et al. | 600/386 |
| 6,073,046 A | 6/2000 | Patel et al. | 600/509 |
| 6,074,345 A | 6/2000 | Van Oostrom et al. | 600/300 |
| 6,076,003 A | 6/2000 | Rogel | 600/390 |
| 6,077,124 A | 6/2000 | Etters et al. | 439/632 |
| 6,083,248 A | 7/2000 | Thompson | 607/30 |
| 6,086,412 A | 7/2000 | Watt et al. | 439/496 |
| 6,093,146 A | 7/2000 | Filangeri | 600/300 |
| 6,102,856 A | 8/2000 | Groff | 600/301 |
| 6,117,076 A | 9/2000 | Cassidy | 300/300 |
| 6,141,575 A | 10/2000 | Price | 600/372 |
| 6,146,190 A | 11/2000 | Fuerst et al. | 439/496 |
| 6,147,618 A | 11/2000 | Halleck et al. | 340/669 |
| 6,149,602 A | 11/2000 | Arcelus | 600/523 |
| 6,154,676 A | 11/2000 | Levine | 607/58 |
| 6,173,198 B1 * | 1/2001 | Schulze et al. | 600/382 |
| 6,198,394 B1 | 3/2001 | Jacobsen et al. | 340/573.1 |
| 6,206,837 B1 | 3/2001 | Brugnoli | 600/529 |
| 6,208,889 B1 | 3/2001 | Gorman | |
| 6,213,942 B1 | 4/2001 | Flach et al. | 600/300 |
| 6,225,901 B1 | 5/2001 | Kail, IV | 340/539 |
| 6,236,874 B1 | 5/2001 | Devlin et al. | 600/372 |
| 6,238,338 B1 | 5/2001 | DeLuca et al. | 600/300 |
| 6,244,890 B1 | 6/2001 | Fuerst et al. | 439/357 |
| 6,267,723 B1 | 7/2001 | Matsumura et al. | 600/300 |
| 6,287,252 B1 | 9/2001 | Lugo | 600/300 |
| 6,289,238 B1 | 9/2001 | Besson et al. | |
| 6,292,687 B1 | 9/2001 | Lowell et al. | |
| 6,295,466 B1 | 9/2001 | Ishikawa et al. | 600/509 |
| 6,304,774 B1 | 10/2001 | Gorman | |
| 6,319,200 B1 | 11/2001 | Lai et al. | 600/300 |
| 6,332,094 B1 | 12/2001 | Gorman | |
| 6,332,940 B1 | 12/2001 | Fujiki et al. | 75/243 |
| 6,364,834 B1 | 4/2002 | Reuss et al. | 600/300 |
| 6,389,308 B1 | 5/2002 | Shusterman | 600/509 |
| 6,416,471 B1 | 7/2002 | Kumar et al. | 600/300 |
| 6,440,067 B1 | 8/2002 | DeLuca et al. | 600/300 |
| 6,441,747 B1 | 8/2002 | Khair et al. | |
| 6,450,953 B1 | 9/2002 | Place et al. | 600/300 |
| 6,475,153 B1 | 11/2002 | Khair et al. | |
| 6,480,733 B1 | 11/2002 | Turcott | 600/516 |
| 6,496,705 B1 | 12/2002 | Ng et al. | |
| 6,533,729 B1 | 3/2003 | Khair et al. | |

| | | | | | | |
|---|---|---|---|---|---|---|
| 2002/0038094 | A1 | 3/2002 | Gorman | 600/520 | WO | WO 00/62667 | 10/2000 |

FOREIGN PATENT DOCUMENTS

| | | |
|---|---|---|
| GB | 2271691 | 4/1994 |
| WO | WO94/01039 | 1/1994 |
| WO | WO97/49077 | 12/1997 |
| WO | WO98/00056 | 1/1998 |

OTHER PUBLICATIONS

Performance Specification sheet published for Motorola C.O.R. HT-220 "Handie-Talkie" FM Radio, printed 1971 by Motorola, 2 pages.

* cited by examiner

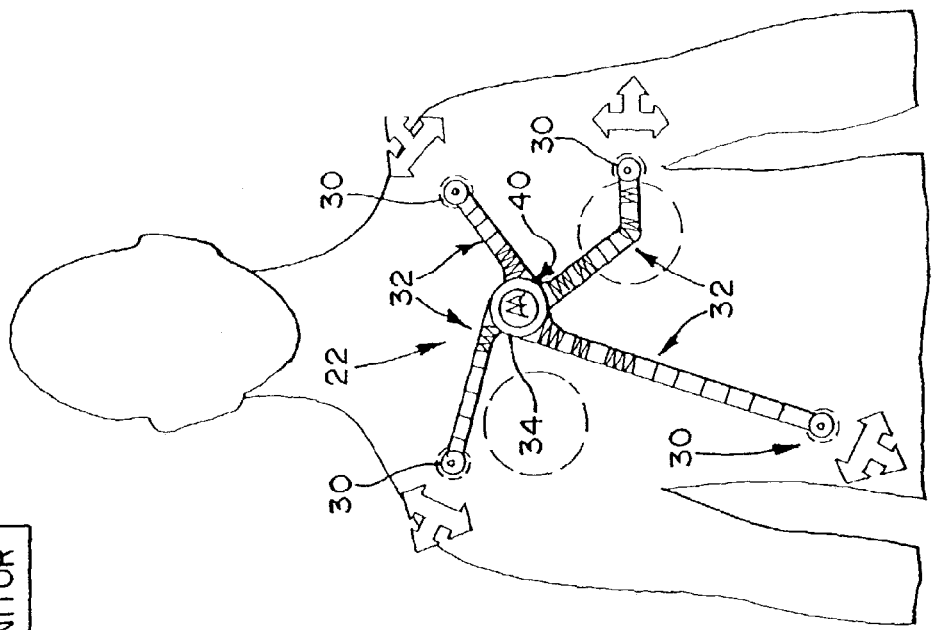
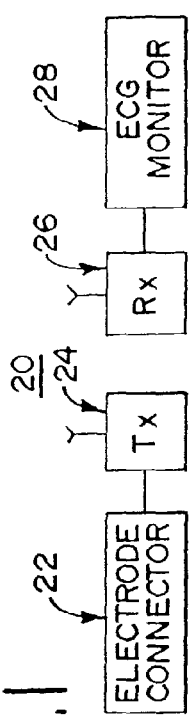
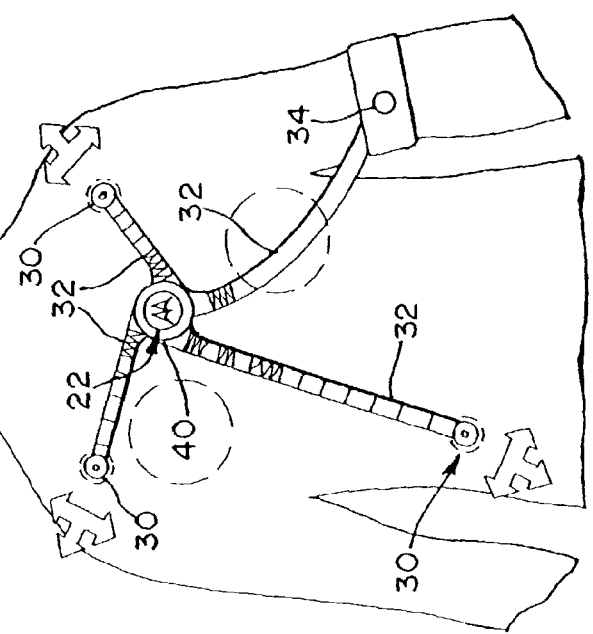
FIG.1
FIG.2A
FIG.2B

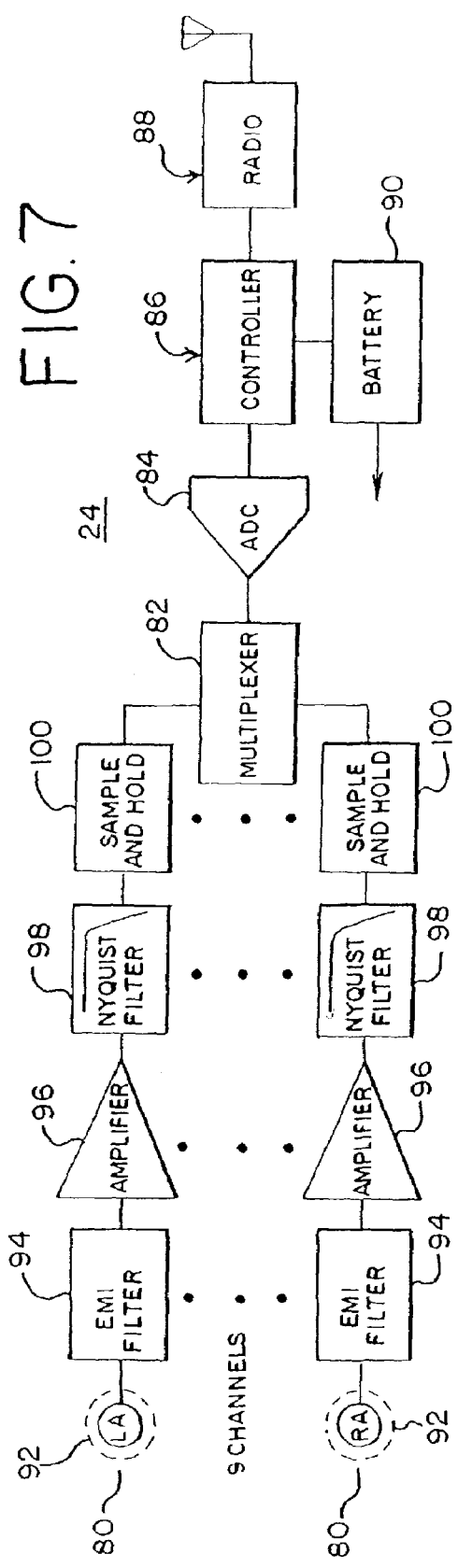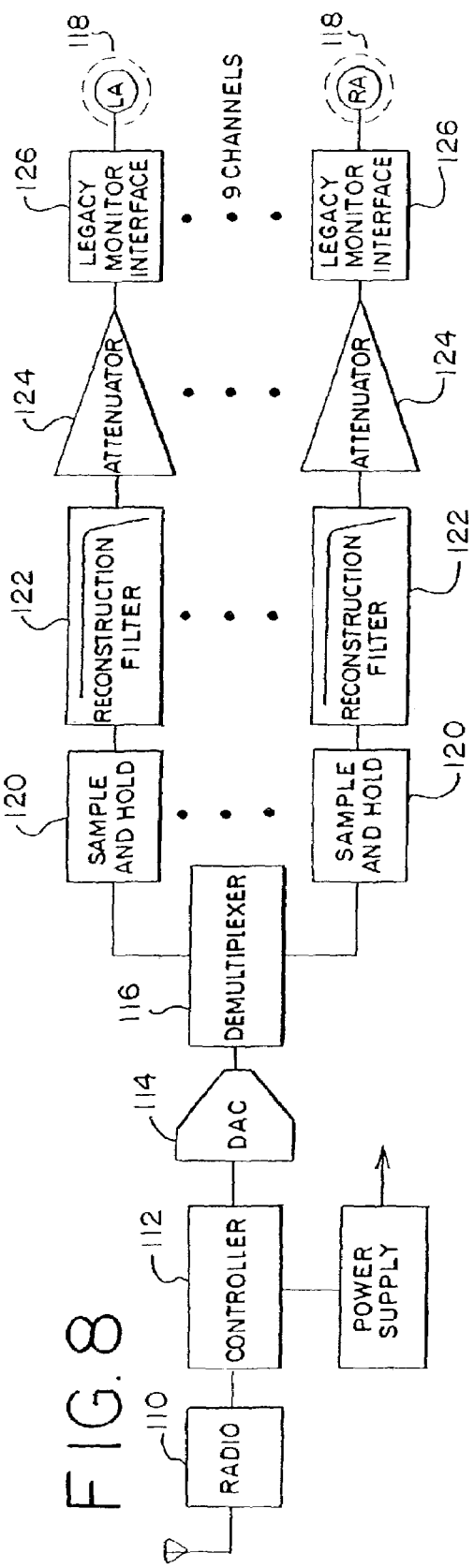

WIRELESS ELECTROCARDIOGRAPH SYSTEM AND METHOD

CROSS-REFERENCE TO RELATED APPLICATIONS

This application is a continuation of U.S. application Ser. No. 09/908,509, filed Jul. 17, 2001, now U.S. Pat. No. 6,611,705 which claims the benefit of the filing date pursuant to 35 U.S.C. §119(e) of Provisional Application Ser. No. 60/219,082, filed Jul. 18, 2000, for a WIRELESS EKG, the disclosures of which are hereby incorporated by reference.

BACKGROUND

This invention relates to medical monitoring systems and methods. In particular, a biomedical system and method for monitoring a patient is provided.

Biomedical monitoring systems include bedside, transportable, ambulatory and discrete vital sign monitors. In vital signs monitors, electrocardiograph (ECG), temperature, blood pressure or other characteristics of a patient are monitored.

ECG systems are used for monitoring activity of a patient's heart. For example, three electrodes are positioned on the patient. The signal from one electrode is used as a reference signal for a difference between the signals of two other electrodes (e.g. ECG vector). By using this reference signal, and a differential amplifier configuration, common mode interference can be essentially eliminated or reduced. As another example, nine electrodes are positioned on the patient for a "12-lead" analysis of electrical activity of the heart.

Wires are connected from the electrodes to an ECG monitor. The ECG monitor processes the signals and outputs ECG data, such as a plurality of traces representing activity of the heart by measuring electrical signals at different positions on the patient. However, the wires inhibit movement by and around the patient. The wires will stress the electrodes, resulting in malfunction or disconnection from the patient. A caregiver's time is then required to reconnect or replace the electrodes. Patients are often moved during a day, requiring disconnecting one ECG monitor and reconnecting another ECG monitor. Often the electrodes also need to be removed and replaced. If not replaced in exactly the same position, the patient's ECG will be different from ECG monitor to ECG monitor, creating an artifact in the ECG.

Wireless ECG systems connect the electrodes to a transmitter to avoid wires from the patient to a monitor. In the example described in WO 94/01039, a microchip is positioned proximate the electrodes on the patient. The microchip analyzes the signals from the electrodes and transmits the results (see page 42). The results are received and provided to a printer or monitor (see page 26). However, a complete system including a monitor, printer or recorder operable to receive the signals as processed by the microchip on the patient is required.

Holter monitors record a patient's vital signs over a time period. The patient carries the complete monitor and recorder. The information can be downloaded or otherwise obtained for subsequent analysis. However, many of these systems limit the bandwidth of signals to suppress artifacts associated with patient movement, so information can be lost. Special monitors or other devices may be required for obtaining the stored data for analysis, preventing maximum use of other equipment.

Wireless ECG systems often use patches or strips for positioning electrodes. The strip is fabricated with a plurality of electrodes electrically connected to the transmitter. If one electrode fails, the entire strip is replaced.

BRIEF SUMMARY

The present invention is defined by the following claims, and nothing in this section should be taken as a limitation on those claims. By way of introduction, the preferred embodiment described below includes a method and system for wireless ECG monitoring.

An electrode connector, transmitter and receiver operate with existing electrodes and ECG monitors. The electrode connector includes connectors for attaching to disposable or reusable single electrodes. The transmitter transmits the signals from the electrodes to the receiver. The receiver passes the electrode signals to the ECG monitor for processing. ECG monitors used with an electrical conductor, for example wire connections to electrodes, are connected with the receiver, avoiding the purchase of a new monitor. Any legacy ECG monitor, including different ECG monitors, connects with the receiver using the ECG monitor's leadwires. The ECG monitor operates as if directly connected to the electrodes without the problems discussed above associated with wires running from the ECG monitor to the patient.

In a first aspect of the invention, an electrode connector for ECG monitoring of a patient is provided. Material is operable to interconnect a plurality of electrodes. The material includes a plurality of electrode releasable connectors.

In a second aspect, a method for connecting electrodes for ECG monitoring is provided. A plurality of electrodes are placed. A plurality of expandable arms, one expandable arm provided for each of the plurality of electrodes, are expanded. The plurality of expandable arms are connected to the plurality of electrodes.

In a third aspect, a system for monitoring electrical signals generated by a patient is provided. A transmitter is operable to transmit electrode signals. A receiver is responsive to the transmitter to generate the electrode signals. The receiver has an output connector operable to connect with electrode wires of an ECG monitor.

In a fourth aspect, a method for monitoring electrical signals generated by a patient is provided. Signals are received from electrodes. Information representing the signals received from electrodes is transmitted. The information is received. The signals received from the electrodes are reconstructed. Existing wires from an ECG monitor are connected. The reconstructed signals are received at the ECG monitor.

In a fifth aspect, a wireless ECG monitoring system for reconstructing signals at a plurality of electrodes is provided. An electrode connector is operable to connect with the plurality of electrodes. A single transmitter is operable to connect with the electrode connector. The single transmitter is operable to transmit signals from the plurality of electrodes. A receiver is operable to reconstruct the signals from the plurality of electrodes.

In a sixth aspect, a method for wireless ECG monitoring with reconstructed signals from a plurality of electrodes is provided. The plurality of electrodes are connected with an electrode connector. Signals from the plurality of electrodes are transmitted with a single transmitter. The signals transmitted by the transmitter are received. The signals from the plurality of electrodes are reconstructed.

Further aspects and advantages of the invention are discussed below in conjunction with the preferred embodiments.

BRIEF DESCRIPTION OF SEVERAL VIEWS OF THE DRAWINGS

FIG. 1 is a block diagram of one embodiment of an ECG monitoring system.

FIGS. 2A-D are front views of various embodiments of electrode connectors and transmitters of the ECG monitoring system of FIG. 1.

FIG. 7 is a block diagram of one embodiment of a transmitter.

FIG. 8 is a block diagram of one embodiment of a receiver.

DETAILED DESCRIPTION OF THE PREFERRED EMBODIMENTS

A wireless ECG system uses existing electrodes and ECG monitors. The wireless ECG system wirelessly bridges between conventional electrodes on a patient and a conventional ECG monitor. The wireless ECG system is an accessory that augments the capability of conventional, or legacy, ECG monitors or systems. The wireless ECG system functions as a wireless extension cord that physically un-tethers a patient from a conventional lead-wire cable connected to a conventional ECG monitor.

The wireless ECG system includes three components: an electrode connector (e.g. sensor array), a transmitter (e.g. ECG-radio) and a receiver (e.g. base station). These components interpose between conventional electrodes worn by a patient and a conventional lead-wire cable of a conventional ECG monitor without requiring any additional changes to the conventional electrodes, the conventional lead-wire cables, or the conventional ECG monitoring systems. An electrode connector with releasable connections, such as snap terminals, and expandable arms electrically connects with existing electrodes, such as snap terminal type electrodes. A transmitter provides signals received from the electrodes to the receiver. The receiver connects to the ECG monitor via conventional lead-wires or electrode wires of the ECG monitor. Signals representing the electrode signals measured or sampled on a patient are provided to the ECG monitor. The existing ECG monitor processes the signal to output ECG data, such as ECG vector data. Consequently, physical coupling between the patient and the electrocardiograph or vital signs monitor is eliminated. This enables the patient to freely ambulate while being monitored by the ECG.

Figure 6:
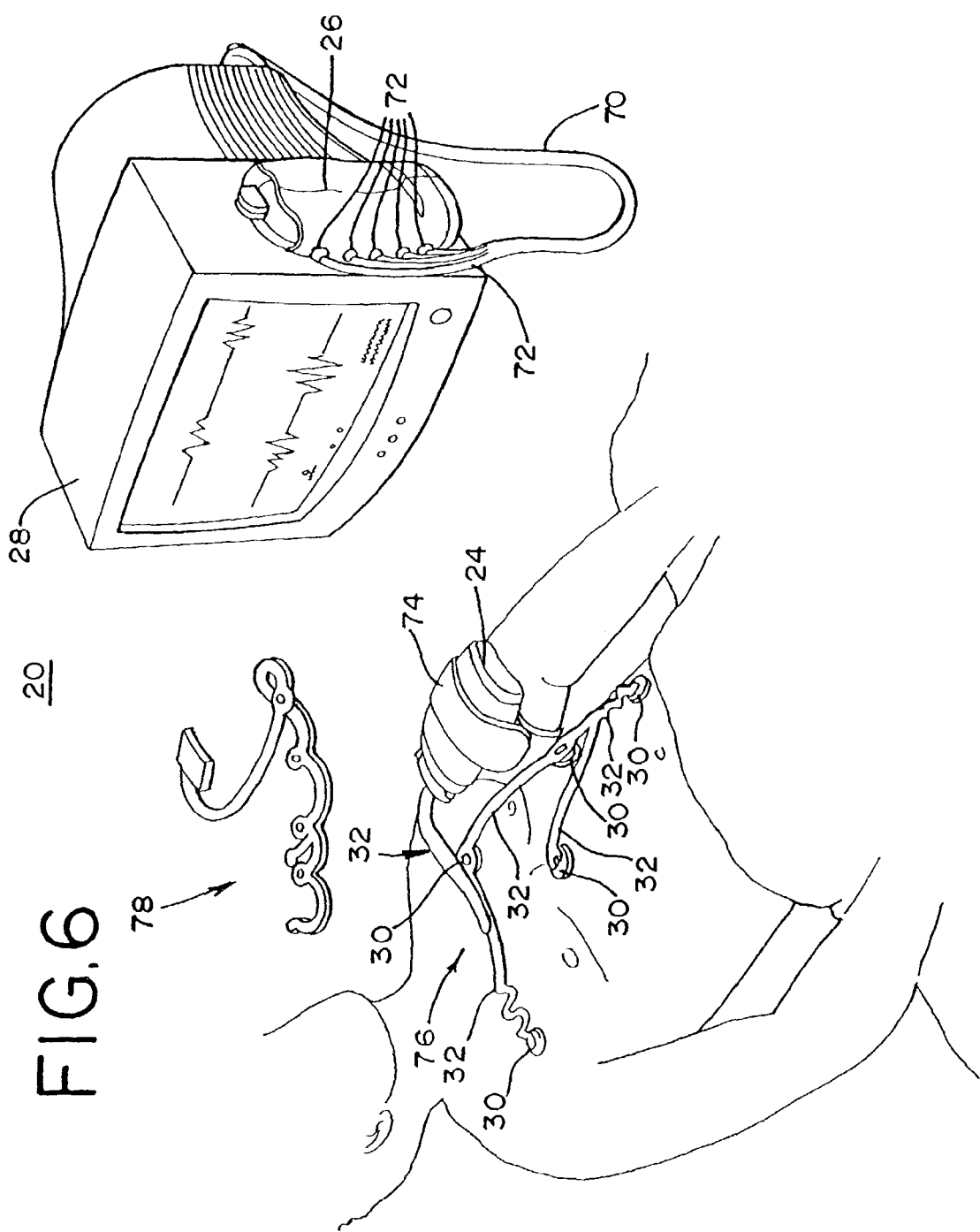
FIG. 6 is a perspective view of another embodiment of an ECG monitoring system.

FIGS. 1 and 6 show a wireless ECG monitoring system 20. The ECG monitoring system 20 includes an electrode connector 22, a transmitter 24, a receiver 26 and an ECG monitor 28. Additional or fewer components can be used, such as providing the system 20 without the ECG monitor. Alternative components can be used, such as a strip or patch with electrodes rather than an electrode connector 22 or a printer rather than an ECG monitor 28.

Figure 2D:
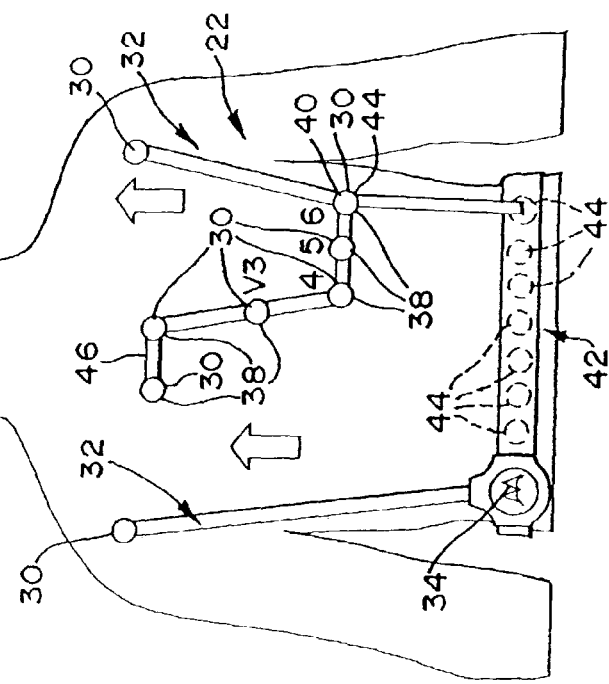
Figure 2C:
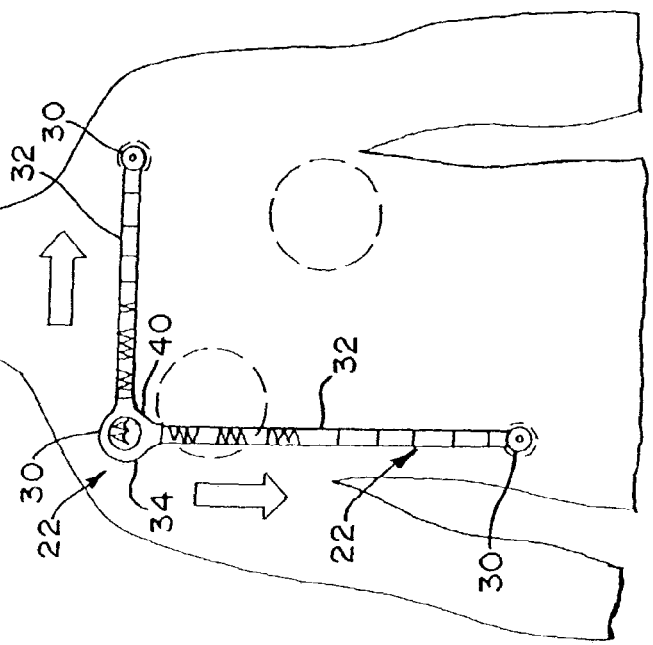

FIGS. 2A-D show electrode connectors 22 of various embodiments used with an array of electrodes 30. The electrodes 30 comprise conductive material. For example, a foam disk with a conductive fabric or a fabric with a conductive metal layer is used. The electrodes 30 include a snap terminal (male, female or both) or tab for connection to a wire. Other connectors may be provided on the electrodes 30. The electrodes 30 are positioned for ECG monitoring, such as positioned for hexaxial-lead monitoring as illustrated in FIGS. 2A-C. For hexaxial-lead monitoring, the electrodes 30 are positioned in left and right arm positions and right and/or left leg positions. With these electrode positions, up to seven leads can be monitored (e.g. Lead I, II, III, aVL, aVR, aVF and chest positions). Other positions of electrodes can be used, such as associated with precordial (e.g. V1-V6) or combinations of hexaxial and precordial (e.g. "12-lead" monitoring). The electrodes 30 are attached to the patient with conductive hydrogel or other adhesives. The electrodes 30 and/or the electrode connector 22 are disposable or reusable.

Figure 3:
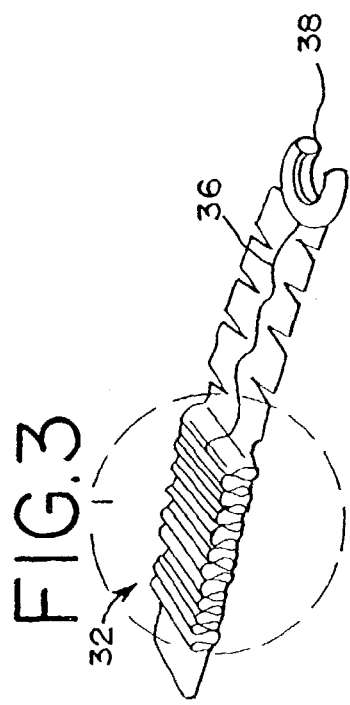
FIG. 3 is a perspective view of one embodiment of an expandable arm of the electrode connectors of FIGS. 2A-D.

The electrode connector 22 includes a plurality of expandable arms 32 and a transmitter 24. The expandable arms 32 comprise polypropylene or polyethylene fabric with an electrically conductive element such as a wire 36 and an electrode joiner 38 as shown in FIG. 3. In one embodiment, the expandable arm 32 is formed from Kapton or Mylar, manufactured by DuPont, a cloth, a fabric or another flexible material. Multiple layers of dielectric, and or electrically or magnetically conductive material can be used to shield the wire 36. Alternatively, no shielding is provided. Fabric or other material can be attached to one or both sides of the expandable arm 32, such as to provide comfort for a patient.

The expandable arm 32 of one embodiment comprises memoryless material, such as the materials discussed above. The expandable arm 32 is die cut in a serpentine pattern as shown in FIG. 3. The expandable arm 32 expands by releasing or breaking connections between portions of the serpentine pattern. When expanded, a portion or all of the expandable arm 32 is extended. Where only a portion of the expandable arm 32 is extended, another portion remains folded or unbroken. Pressure on the electrode 30 from elastic or stretchable material is avoided, providing for more stable connection of the electrode 30 to the patient. The expandable arm 32 also allows for extension as needed without extra extension and resulting loose material to be tangled or provide discomfort. In alternative embodiments, a stretchable or elastic expandable arm 32 is used. In yet other alternative embodiments, a non-expandable arm is used.

The electrical conductor or wire 36 in the expandable arm 32 preferably comprises a conductor printed on the Mylar, Kapton or other flexible dielectric material. The printed conductor is flexible, providing electrical connection between the electrode 30 and the transmitter 24 whether expanded or unexpanded. In alternative embodiments, the wire 36 comprises a thread of copper or another conductive material. In yet other embodiments, the wire comprises a coaxial cable. One or more wires 36 are provided for each electrode 30. For some expandable arms 32, one wire 36 electrically connects from one electrode 30 to the transmitter 24 or another expandable arm 32. For other expandable arms 32, a plurality of wires 36 connect from a respective plurality of electrodes 30 on the same and/or another expandable arm 32.

The electrode joiner 38 comprises a clip (e.g. alligator clip), snap terminal, or connector (male, female or both), adhesive tab or other device for electrically and physically joining the electrode 30 to the expandable arm 32. As shown in FIG. 2D, a plurality of electrode joiners 38 can be used on one expandable arm 32. In other embodiments, one electrode joiner 38 is provided at an end or other portion of the expandable arm 32. If one electrode 30 malfunctions, only the electrode 30 is removed and replaced. The electrode connector 22 is kept.

The other end of the expandable arm 32 connects with other expandable arms 32 or the transmitter 24. The plurality of expandable arms 32 are connected in any of various configurations, such as a spiral configuration shown in FIGS. 2A and 2B. The expandable arms 32 releasably or fixedly connect from a hub 40. In the embodiment of FIG. 2A, one expandable arm 32 includes wires for all or a sub-set of the electrodes 30 to electrically communicate with the transmitter 24. The transmitter 24 is spaced away from the hub 40, such as being positioned on an arm band (shown), or on another location on the patient. For example, FIG. 6 shows the transmitter 24 held to the patient with an arm band 74 comprising neoprene or other fabric. In the embodiment of FIG. 2B, the transmitter 24 is positioned on the hub 40.

The hub 40 comprises the same material as the expandable arms 40, such as from using a continuous sheet to form the hub 40 and expandable arms 32. In other embodiments, the hub 40 comprises the same or different material with releasable connectors for electrically and physically connecting with the expandable arms 32. For example, the hub 40 comprises plastic or other material with plurality of conductive snap terminals for connecting with the expandable arms.

Another configuration is a "7" or "L" configuration, such as the embodiment shown in FIG. 2C. One of the electrode positions generally corresponds to the hub 40, and expandable arms 32 expand from the hub 40. Other alternative configuration embodiments include "C" or "U" shapes with multiple hubs.

Figure 4:
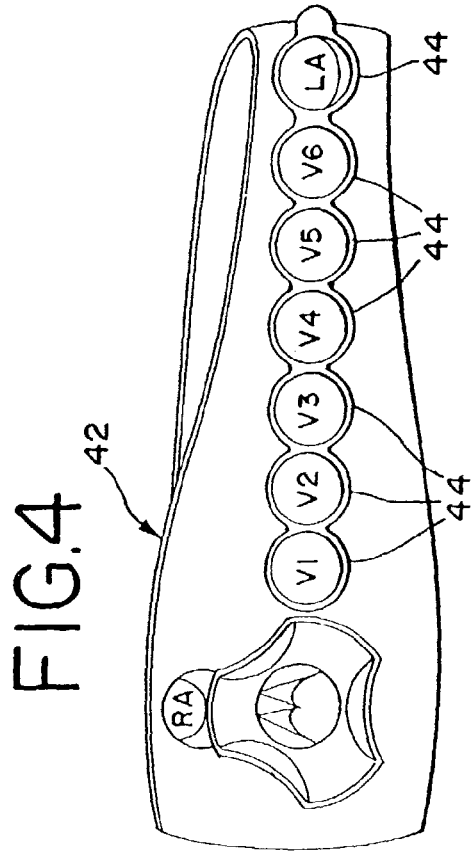
FIG. 4 is a front view of one embodiment of a belt used with the electrode connector of FIG. 2D.

Yet another configuration is shown in FIG. 2D. A belt 42 connects with a plurality of expandable arms 32. The belt 42 comprises neoprene, non-woven polypropylene or polyethylene fabric or other materials. One or more pockets or connectors for the transmitter 24, other electrical components, batteries, displays, or other devices are provided on the belt 42. In one embodiment shown in FIG. 4, the belt 42 is formed to fasten or stretch around a waist of the patient, but arm, neck, chest or leg belts can be used. One or more of the expandable arms 32 releasably connects with the belt 40. In one embodiment, the belt 40 includes separate connectors 44 for each electrode position. In other embodiments, one or more of the connectors 44 on the belt 40 include separate electrical contacts for electrically connecting with multiple wires 36 and associated electrodes 30 on one expandable arm 32. The connectors 44 are provided on the outer surface of the belt 42, but can be provided in pockets. The transmitter 24 is positioned on the belt 42 or elsewhere on the patient.

As shown in FIG. 2D, one or more of the expandable arms 32 may include one or more connectors 44 for connecting with other expandable arms 32, forming a hub 40. For example, an electrically conductive snap terminal or terminals connect the expandable arms. Other connectors, such as male and female housings with clips and wires associated with connecting multiple separate wires between the expandable arms, can be used.

The configuration is associated with the desired ECG monitoring. FIGS. 2A-C illustrate hexaxial positions for the electrodes 30, such as associated with continuous monitoring. Electrodes 30 are positioned at hexaxial positions associated with left arm, right arm, left leg and/or right leg. Many ECG systems use three electrode positions, but some use four or more. FIGS. 2A and 2C show three electrode positions. FIG. 2B shows four electrode positions. More or fewer electrode positions, such as three to five positions, may be provided with additional electrode joiners 38 and/or expandable arms 32.

FIG. 2D shows both hexaxial and precordial positions for the electrodes 30, such as associated with "12 lead" ECG monitoring. Two or more expandable arms 32 connect with electrodes 30 in hexaxial positions. One or more expandable arms 32, such as expandable arm 46, connect with electrodes 30 in precordial positions. In this embodiment, the precordial expandable arm 46 connects with another of the expandable arms 32 used for hexaxial positions. The resulting hub 40 is associated with one of the precordial electrode positions. In alternative embodiments, the hub 40 is spaced away from any electrode 30. In yet other alternative embodiments, the precordial expandable arm or arms 46 separately connect with the belt 42. For example, separate hexaxial and precordial electrode connectors 76 and 78 are provided as illustrated in FIG. 6. The precordial electrode connector 78 connects with the hexaxial electrode connector 76 or the transmitter 24.

The hubs 40 and expandable arms 32 may include connectors 44 for adding additional expandable arms 32 or electrodes 30. For example, two or more expandable arms 32 are positioned for hexaxial-lead monitoring as shown in FIG. 2D without the precordial expandable arm 46. When precordial-lead monitoring is desired, electrodes 30 are positioned along six precordial positions, and the expandable arm 46 is expanded and connected with the precordial electrodes 30. The expandable arm 46 is also connected to the belt 42 or other expandable arm 32. Alternatively, different electrode connectors 22 are used for different ECG systems or numbers of electrodes. Since the expandable arms 32 are flexible and expandable, the same electrode connector 22 is used for various electrode positions as represented by the bold arrows in FIGS. 2A-D.

The transmitter 24 receives the signals from the electrodes 30. The transmitter 24 comprises a wireless transmitter or transceiver, such as a radio, ultrasound, infrared or other transmitter. For example, a transceiver operable according to Bluetooth specifications (i.e. a Bluetooth transceiver) is used. In one embodiment, the transmitter 24 comprises an application specific integrated circuit, a processor or other circuit.

FIG. 7 shows one embodiment of the transmitter 24. The transmitter 24 includes a plurality of electrode signal channels 80, a multiplexer 82, an analog-to-digital converter (ADC) 84, a controller 86, a radio 88 and a battery 90. Additional, fewer or different components can be used. The battery 90 comprises a replaceable or rechargeable lithium battery connected to provide power to the various components of the transmitter 24.

In one embodiment, nine electrode signal channels 80 corresponding to the typical nine electrodes used for hexaxial-lead and precordial-lead monitoring are provided. Fewer or additional electrode signal channels 80 can be provided. The electrode signal channels 80 each comprise a connector 92, a filter 94, an amplifier 96, a Nyquist filter 98 and a track and hold circuit 100. The connector 92 comprises snaps, plugs or other electrical connectors for connecting with the wires 36. The filter 94 comprises a low pass filter, such as for removing electromagnetic interference signals. The amplifier 96 amplifies the signals from the electrodes 30. The Nyquist filter 98 comprises a low pass filter for removing high frequency content of the amplified signals to avoid sampling error. The track and hold circuit 100 enables the system to sample all 9 channels of signals at a same or relative times so that there is no differential error created when these signals are combined later in a legacy ECG monitor.

The multiplexer 82 sequentially selects signals from the electrode signal channels 80 using time division multiplexing, but other combination functions can be used. The ADC 84 converts the combined analog signals to digital signals for transmission. The controller 86 controls operation of the various components and may further process the digital signals, such as diagnosing operation, controlling any user interface (e.g. input and/or output devices), and detecting connection to electrodes. Preferably the controller comprises a digital signal processor (DSP) that decimates the digitized signals so as to lessen the bandwith required to transmit the signals. The radio 88 modulates the digital signals with a carrier signal for transmission. In one embodiment, the radio 88 includes a demodulator for receiving information. The controller 86 processes the received information.

In one embodiment, the transmitter 24 is operable to minimize introducing undesired noise or signals. For example, components are matched such that later application to a differential amplifier in a legacy ECG monitor for determining a heart vector is accurate. In one embodiment, the ECG vectors are not formed by the ECG system 20, but rather by the legacy ECG monitor. Because the ECG system 20 is essentially "in-series" with the legacy ECG monitor, any error may produce undesirable results. One potential source of error is differential error. This differential error can be observed on the legacy ECG monitor when the ECG monitor forms the ECG lead signals by combining the individual electrode signals in the ECG monitor input stage. This input stage comprises a difference, or differential, amplifier to eliminate common mode interference from the signals produced at the electrodes 30. If there is any difference in how each of the electrode signals are processed, when the legacy ECG's differential amplifier forms the ECG lead signals or ECG vectors an artifact will be present. For example, in the transmitter 24 if there is a difference in the gain of the amplifiers, a difference in the phase shift associated with the anti-aliasing (Nyquist) filters, a difference in how the respective track and hold circuits treat the electrode signals, this differential error creates an artifact on the legacy ECG monitor. One important technique to minimize this potential source of differential error, is to choose a Nyquist filter 98 cutoff frequency that is very high. This is because each individual filter will have differing group delay performance, and to mitigate that difference the frequency that this group delay will affect is much higher than the frequency of the ECG signals, which are about 0.05 Hz to 150 Hz. By choosing a high cutoff frequency for the Nyquist filters 98, any mismatch in the Nyquist filter 98 components will not affect accuracy of the individual electrode ECG signals. For example picking a filter cutoff frequency of 1,200 Hz mitigates this source of error. With this approach, the individual electrode ECG signals are oversampled at about 3,000 Hz in order to not introduce aliasing. Of course higher filter cutoff frequencies and correspondingly higher sampling rates may further reduce error. Lower cutoff frequencies and/or sampling rate may be used.

Because the electrode signals are now sampled at such a high rate, these signals may be decimated to minimize the required transmission bandwidth. For example the digital samples are decimated by a factor of 8 in the controller 86. Greater or lesser rates of decimation can be used, such as decimation as a function of the bandwidth available for transmission, the number of electrode signals to be represented, and the Nyquist sampling rate. In alternative embodiments, the digital data is compressed, the electrode signals are not oversampled, or no decimation is provided.

The selected signals are transmitted as radio or other signals modulated with a carrier signal. Various formats for transmission can be used, such as Bluetooth, TCP/IP, or other formats. The controller 86 controls the acquisition and transmission of the electrode signals. The transmitted signals comprise data representing the signals received from the electrodes 30. In alternative embodiments, the controller 86 may also processes the signals prior to transmission, so the transmitted signals comprise ECG vector data. In one embodiment, the transmitter 24 also receives control information from the receiver 26, such as instructions to resend signals.

The transmitter 24 is positioned near the patient. In the embodiment shown in FIGS. 2A and 2C, the transmitter 24 is positioned on the hub 40 or an expandable arm 32. In the embodiment shown in FIG. 2B, the transmitter 24 is positioned on an arm band, but leg, chest or other bands can be used. In the embodiment of FIG. 2D, the transmitter 24 is positioned on the belt. Either a pocket or a surface mount is provided for the transmitter 24. In alternative embodiments, the transmitter 24 is positioned in a pocket of clothing or elsewhere on the patient.

In one embodiment, the transmitter 24 is removable. For example, clips, screws, bolts, latches or other devices releasably hold the transmitter 24 in contact with the electrode connector 22. Electrical contact is provided by connectors operable to withstand electrical energy produced by a defibrillator. These connectors may also provide the physical connection. The transmitter 24 is removed for recharging the battery or a plug is provided on the electrode connector 22 or the transmitter 24 for recharging the battery without removal. The battery or the transmitter 24, like the electrode connector 22, can be used for multiple days or multiple times and is separately disposable to avoid costly replacement of the entire system 20.

Referring to FIGS. 1 and 6, the receiver 26 receives the transmitted signals. The receiver 26 comprises a radio, infrared, ultrasound or other receiver. An application specific integrated circuit, digital signal processor or other circuit for receiving signals from the transmitter 24, decoding the received signals, and generating representative electrode signals is used. In one embodiment, the receiver comprises a transceiver for two-way communication with the transmitter 24. For example, a transceiver operable pursuant to the Bluetooth specification is provided.

FIG. 8 shows one embodiment of the receiver 26. The receiver 26 includes a radio 110, a controller 112, a digital-to-analog converter (DAC) 114, a demultiplexer 116, a plurality of electrode signal channels 118 and a battery or power supply 120. Additional, fewer or different components can be used. Preferably, the power supply 120 comprises a replaceable or rechargeable battery or other power source connected to provide power to the various components of the receiver 26.

The radio 110 demodulates the received signals for identifying digital data representing the combined electrode signals. In one embodiment, the radio 10 also includes a modulator for transmitting control information. The controller 112 controls operation of the various components and may further process the signals from the radio 110, such as interpolating data, converting the signals to digital information, generating control signals for the transmitter 24, operating any user interface, operating any user output or input devices, and diagnosing operation of the system 20. Preferably, the controller 112 in the receiver 26 interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest, i.e. less than 150 Hz. The DAC 114 converts the digital signals to analog signals. The demultiplexer 116 separates the individual regenerated electrode signals onto the separate electrode signal channels 118.

In one embodiment, nine electrode signal channels 118 corresponding to the typical nine electrodes used for hexaxial-lead and precordial-lead monitoring. Fewer or additional electrode signal channels 118 can be provided. The electrode signal channels 118 each comprise a sample and hold circuit 120, a filter 122, an attenuator 124 and a connector 126. The sample and hold circuit 120 is controlled by the controller 112 so that the converted electrode signals appear simultaneously on each electrode signal channel 188. Differential error may be mitigated. Other embodiments may include individual DAC's that provide the signals substantially simultaneously. The filter 122 comprises a low pass reconstruction filter for removing high frequency signals associated with the DAC conversion process. The attenuator 124 comprises an amplifier for decreasing the amplitude to a level associated with signals at the electrodes 30, that were earlier amplified in the amplifiers 96 of the transmitter 24. This results in a unity system gain so as not to introduce error between the electrodes and the legacy ECG monitor. Other gains may be used. The connector 126 comprises posts, snaps, plugs, tabs or other electrical connectors for connecting with the lead wire set 70.

The controller 112 sets the demodulation frequency in response to input from the user input device or memory, or the demodulation frequency is fixed. In one embodiment, the user input comprises buttons associated with manual frequency control, with preprogrammed channels, with numbers or characters, with possible transmitters 24 or other input devices for selecting a demodulation frequency. The receiver 26 electrically connects to the ECG monitor 28.

FIG. 6 shows one embodiment of the wireless ECG system 20 where the wires 70 from a standard ECG monitor 28 attach to the electrically conductive posts 72 or other connectors on the receiver 26. The wires 70 comprise a lead-wire set, cable or electrode connectors from or for the ECG monitor 28. The posts 72 are labeled as electrodes 30, and the wires 70 are connected with corresponding outputs on the receiver 26. The receiver 26 outputs signals as if from the corresponding electrodes 30 for processing by the ECG monitor 28. In alternative embodiments, the receiver 26 includes wires for connecting with the ECG monitor 28.

In one embodiment, the receiver 26 physically connects to the ECG monitor 28. For example, latches, clips or straps on the receiver 26 connect the receiver 26 to the ECG monitor 28. In alternative embodiments, the receiver 26 connects to an equipment pole or wall or is free standing. The receiver 26 may be releasably attached. When a patient is moved, the receiver 26 may be detached and moved adjacent a different ECG monitor. Alternatively, different receivers 26 operate with the same transmitter 24, so another receiver 26 is programmed to receive signals from the transmitter 24 on the patient.

The ECG monitor 28 comprises one or more of a bedside monitor, a transport monitor or a discrete (i.e. diagnostic) monitor. Bedside and transport monitors are used for continuous monitoring, such as associated with hexaxial-lead monitoring. A discrete monitor typically is used periodically for analysis, such as associated with "12-lead" monitoring or obtaining multiple vectors associated with precordial and/or hexaxial leads. The ECG monitor 28 processes the electrode signals as if the signals where received directly from the electrodes 30. Neither of the transmitter 24 or receiver 26 includes differential amplifiers for determining a heart vector associated with two electrodes.

Some ECG monitors 28 test for failure or malfunction of electrodes 30. For example, a signal is output on the lead wire to the electrode 30 or a direct current level associated with the signal from the electrode 30 is monitored. To continue to provide this functionality, the wireless ECG system 20 tests for electrode failure or malfunction and indicates the results to the ECG monitor 28. For example, the transmitter 24 performs the same or similar tests as the ECG monitor 28. In other embodiments, the transmitter 24 or receiver 26 determines whether the ECG signal is within an expected range. For example, the controller 112 (FIG. 8) compares the digital electrode signals, such as after interpolation, to maximum and minimum thresholds. If either threshold is exceed by a particular number of samples or for a particular time, a lead-off or faulty electrode 30 is indicated. When one or more samples are subsequently within hysteresis limits of the thresholds, then an error is no longer indicated. When a lead-off condition is indicated, the receiver 26 opens an analog switch or, alternatively does not generate a signal for the output corresponding to the malfunctioning or failed electrode 30. As a result, the ECG monitor 28 indicates a failure of the electrode 30. If the transmitter 24 and receiver 26 are out of radio communication range, a lead-off condition is presented to the ECG monitor 28.

Figure 5:
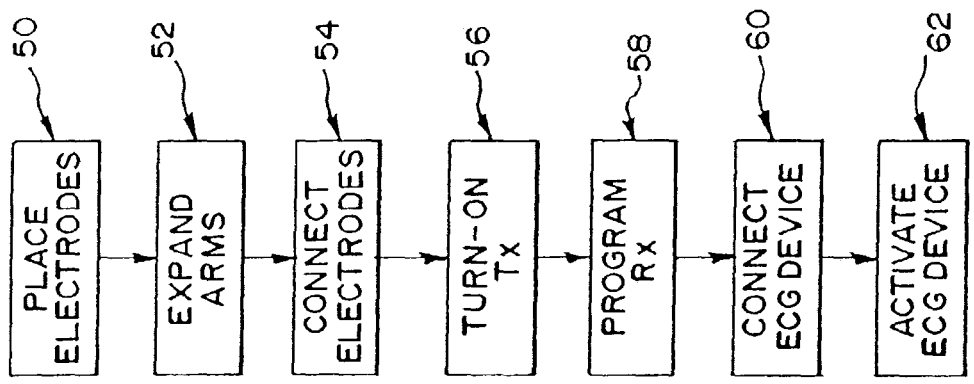
FIG. 5 is a flow chart of one embodiment for operation of the ECG monitoring system of FIG. 1.

The ECG monitoring system 20 is used for continuous hexaxial-lead or occasional precordial-lead or both hexaxial-lead and precordial-lead monitoring. FIG. 5 shows the acts representing use of the system 20

In act 50, the electrodes 30 are positioned on the patient. For example, electrodes 30 are positioned in hexaxial positions, precordial positions or combinations thereof.

In act 52, the electrode connector 22 and transmitter are positioned. The expandable arms 32 are expanded, such as expanding a portion or all of the expandable arms 32. Another portion of the expandable arms 32 may remain folded or unexpanded. The expandable arms 32 are expanded to reach one or more electrodes.

In act 54, the electrode connector 22 is connected with the electrodes 30. For example, the expandable arms 32 are releasably connected with one or more electrodes 30, such as snapping or clipping to the electrodes 30. Expandable arms 32 may also be connected with other expandable arms 32, hubs 40, the transmitter 24, and/or the belt 42. In an alternative embodiment, the electrodes 30 are connected with the electrode connector 22 prior to positioning the electrodes 30 and expanding the expandable arms 32.

In act 56, the transmitter 24 is operated or turned-on. In one embodiment, a switch on the transmitter 24 activates the transmitter. In alternative embodiments, connection to one or more of the wires 36, expandable arms 32, electrode connecter 22 and/or electrodes 30 activates the transmitter 24. In response, the transmitter 24 radiates a signal representing the electrode signals.

In act 58, the receiver 26 is programmed. A code corresponding to the transmitter 24 is entered, or a channel (i.e. frequency) is selected. In an alternative embodiment, the receiver 26 searches a plurality of frequencies for an appropriate signal, such as a signal in an expected format or with a particular code. If more than one signal is identified, an output may be provided for user selection of the appropriate signal. A visual or audible output indicating reception of a signal may be provided.

In act 60, wires or electrode connectors from the ECG monitor 28 are connected to the receiver 26. In alternative embodiments, act 60 occurs before any of acts 50, 52, 54, 56 or 58.

In act 62, the ECG device, such as a monitor, printer or memory, is activated. Analog or digital signals corresponding to signals at the electrodes 30 are received by the ECG device from the receiver 26. The ECG device processes the signals to generate ECG data, such as one or more heart vectors.

In one embodiment, a light emitting diode, a light pipe or multiple light emitting diodes, or other output device is provided on the transmitter 24 and/or one or more of the expandable arms 32. The output device indicates electrical operation of the transmitter or conductance of signals by the wire 36. Different output devices may represent improper operation. In one embodiment, extending the expandable arm 32 activates operation of the output device or devices.

The wireless ECG system 20 provides for fewer artifacts due to wire movement, allows the patient to wear clothing without interfering with wires, and provides less psychological intimidation of the patient due to wire connections to a machine. The electrodes 30 are less likely to disconnect because of lower mass or force due to wires connected to the ECG monitor 28. The wireless ECG system 20 is usable with many different ECG monitors 28 and electrodes 30. Faster setup when a patient is transferred and connected to a different ECG monitor 28 is provided since the same electrodes 30 already positioned on the patient can be used. Since the electrodes 30 are not repositioned due to a transfer, the ECG monitor output is more comparable to the output of previous ECG monitors. If an electrode 30 fails because of patient movement or perspiration, the electrode can be replaced without replacing the electrode connector 22 or other electrodes 30.

While the invention has been described above by reference to various embodiments, it will be understood that many changes and modifications can be made without departing from the scope of the invention. For example, the transmitter and receiver may each comprise transceivers for two-way communication and control. Various aspects can be used with or without other aspects, such as using the electrode connector 22 with a transmitter that processes the electrode signals into ECG vector data rather than transmitted signals representing the electrode signals. Another example is transmitting the electrode signals but using a different electrode connector, strip, patch or mere wires. Other biomedical systems, such as temperature or blood pressure, can be additionally or alternatively monitored using the systems and methods discussed above.

It is therefore intended that the foregoing detailed description be understood as an illustration of the presently preferred embodiments of the invention, and not as a definition of the invention. It is only the following claims, including all equivalents that are intended to define the scope of this invention.

What is claimed:

1. An electrode connector for physiological monitoring of a patient, the connector comprising:

material operable to interconnect a plurality of electrodes; and a plurality of electrode connectors provided on the material, the connectors being releasable and rejoinable;

wherein the material comprises a plurality of arms, each of the plurality of arms corresponding to respective ones of the plurality of electrode connectors and wherein the plurality of arms are configured relative to each other to aid in positioning the plurality of electrode connectors on the patient.

2. The electrode connector of claim 1 wherein the electrode connectors are adapted to withstand the electrical energy produced by a defibrillator used on the patient.

3. The electrode connector of claim 1 wherein the plurality of arms comprise at least four arms associated with hexaxial electrodes, the at least four arms connected at angles to each other, the angles corresponding to relative hexaxial positions on the patient.

4. The electrode connector of claim 1 wherein each of the plurality of arms include an electrical conductor.

5. The electrode connector of claim 4 wherein each of the electrical conductors electrically connects with the respective electrode connector.

6. The electrode connector of claim 1 wherein at least a first of the plurality of arms corresponds to a hexaxial electrode position and at least a second of the plurality of arms corresponds to a precordial electrode position, the first and second arms being connected such that each of the first and second arms is disposed towards the corresponding electrode positions.

7. The electrode connector of claim 6 wherein the second arm connects to the first arm.

8. The electrode connector of claim 1 further comprising a belt, and wherein at least one of the plurality of arms is expandable, the at least one expandable arms connecting with the belt.

9. The electrode connector of claim 8 wherein a first arm comprises a hexaxial electrode arm connected with the belt and a second arm comprises a hexaxial and precordial electrode arm connected with the belt, the first and second arms connected with the belt such that the first arm extending from the belt to a first hexaxial electrode position avoids intersection with the second arm extending from the belt to a second hexaxial and a first precordial electrode positions.

10. The electrode connector of claim 1 wherein each of the plurality of arms extends from a central position to corresponding electrode positions without intersection, each of the plurality of arms being extendable and comprising a memoryless material.

11. The electrode connector of claim 1 further comprising a releasable arm connector on at least one of the plurality of arms, the releasable arm connector spaced away from at least one of the plurality of electrode connectors associated with the one arm.

12. A method for connecting electrodes for ECG monitoring, the method comprising the acts of:

(a) placing a plurality of electrodes onto a patient in preselected positions;

(b) positioning a plurality of arms, one arm provided for each of the plurality of electrodes, the plurality of arms connected or connectable relative to each other to align with the preselected position of each of the plurality of electrodes;

(c) connecting the plurality of arms to the plurality of electrodes, respectively; and (d) connecting a precordial-lead arm with a hexaxial-lead expandable arm.

13. The method of claim 12 wherein (a) comprises placing the plurality of electrodes for hexaxial-lead monitoring, the preselected positions being hexaxial electrode positions.

14. The method of claim 12 wherein (a) comprises placing the plurality of electrodes for precordial-lead monitoring, the preselected positions being precordial electrode positions.

15. The method of claim 12 wherein (a) comprises placing the plurality of electrodes for both hexaxial-lead and precordial-lead monitoring, the preselected positions being hexaxial and precordial positions.

16. The method of claim 12 further comprising:
(d) transmitting signals from the plurality of electrodes with a radio.

17. The method of claim 12 wherein (c) comprises electrically connecting the plurality of electrodes to the plurality of arms with a snap terminal.

18. The method of claim 12 wherein (b) comprises positioning the plurality of arms at different angles from a central hub.

19. The method of claim 12 further comprising:
(d) connecting at least one of the plurality of arms to a belt.

* * * * *